United States Patent [19]

Mirabella

[11] 4,262,204
[45] Apr. 14, 1981

[54] PATIENT CRADLE FOR COMPUTERIZED TOMOGRAPHY APPARATUS

[75] Inventor: Paul J. Mirabella, Waukesha, Wis.

[73] Assignee: General Electric Company, Schenectady, N.Y.

[21] Appl. No.: 78,422

[22] Filed: Sep. 24, 1979

[51] Int. Cl.³ .............................................. G03B 41/16
[52] U.S. Cl. ............................. 250/445 T; 250/439 R
[58] Field of Search ........................ 250/439 R, 445 T

[56] References Cited
U.S. PATENT DOCUMENTS

| | | | |
|---|---|---|---|
| 3,449,570 | 6/1969 | Kok | 250/439 R |
| 3,897,345 | 7/1975 | Foster | 250/439 R |
| 3,947,686 | 3/1976 | Cooper | 250/439 R |
| 4,115,696 | 9/1978 | Truscott | 250/445 T |

*Primary Examiner*—Craig E. Church

[57] ABSTRACT

A cradle, adapted for being extended from a base in cantilever fashion to support a patient in the x-ray beam of a computerized tomography scanner, is composed of an elongated x-ray permeable structural foam core having a generally crescent-shaped cross section with small radius edges. The core is encased in a resin-based preferably carbon fiber filled skin, formed with smaller radius edges.

2 Claims, 7 Drawing Figures

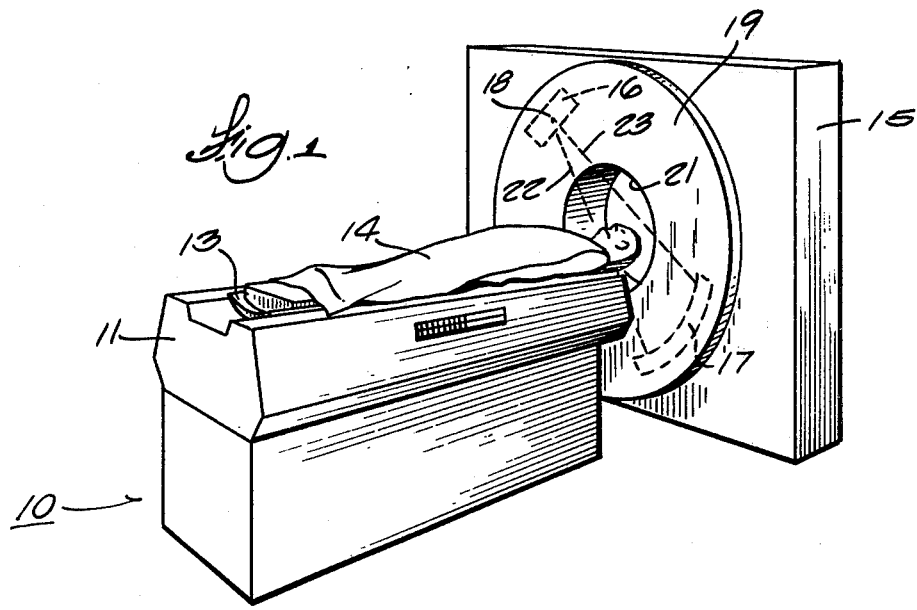
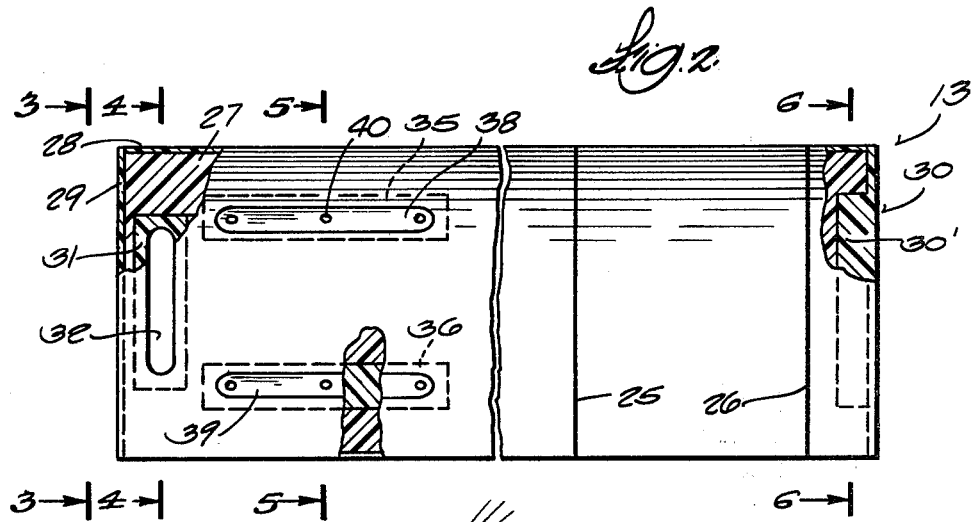
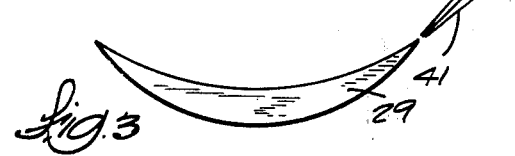
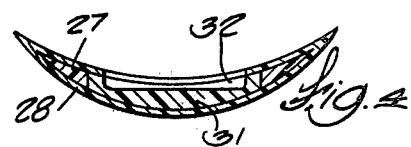
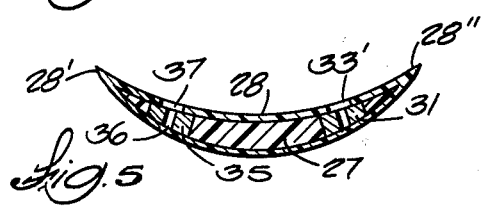
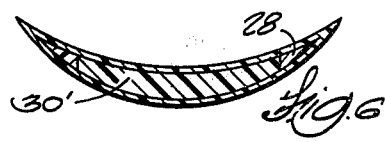

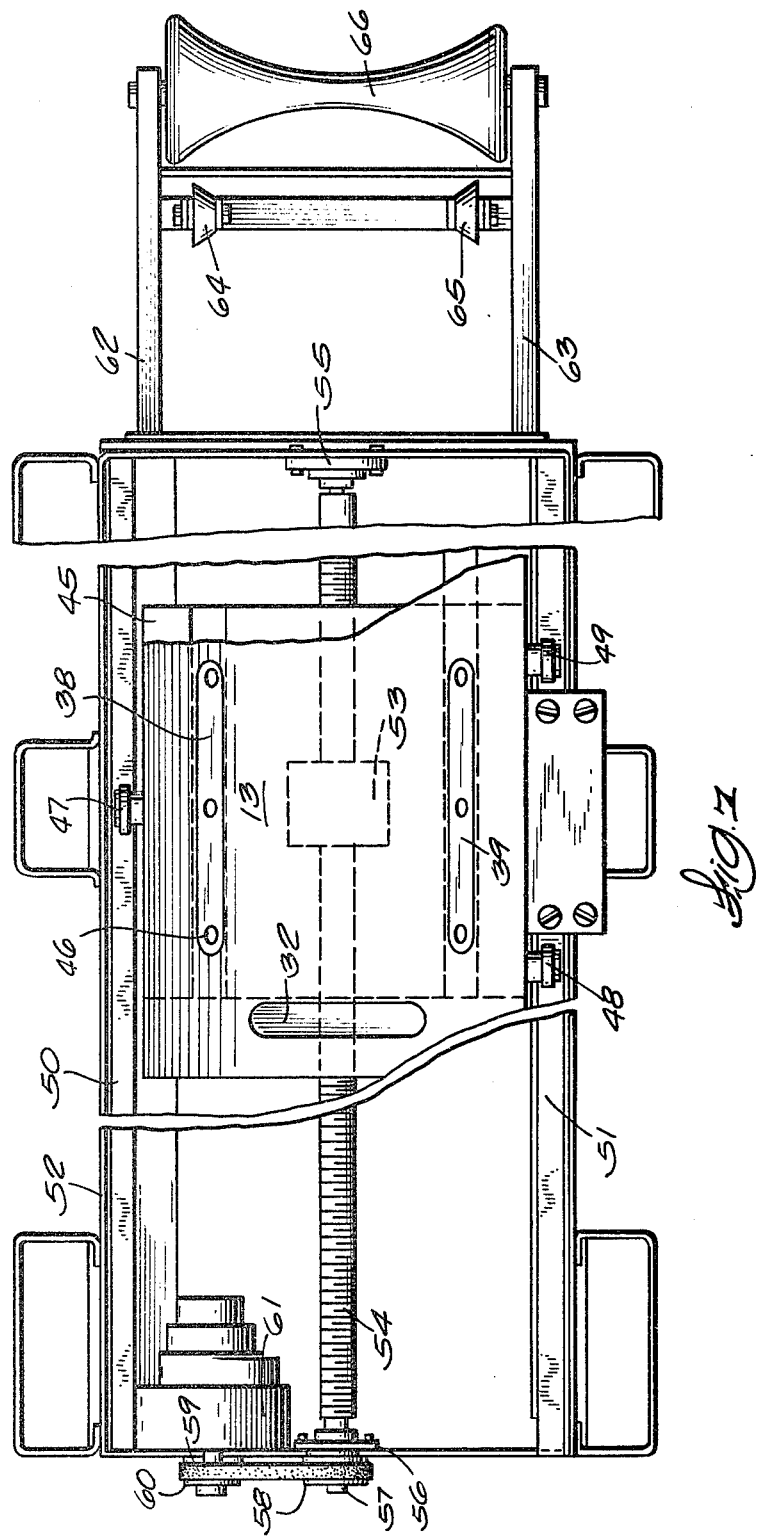

PATIENT CRADLE FOR COMPUTERIZED TOMOGRAPHY APPARATUS

This invention relates to a cradle or table top for supporting a patient for being scanned with an x-ray beam in computerized tomography apparatus.

As is known, computerized tomography involves supporting a patient between an x-ray source and a detector and rotating or translating the source and detector jointly to obtain a set of x-ray attenuation data which can be used for reconstructing a visible image of a body layer that can be viewed in axial perspective on a cathode ray tube screen. Computerized tomography systems are capable of distinguishing very small x-ray attenuation differences and, hence, density differences in the anatomy being scanned. It is, therefore, important to have the body of the patient supported on a table or cradle which has low and uniform x-ray attentuation characteristics or the subtle density differences in the anatomy will become undistinguishable from the density differences in the cradle. On the other hand, the cradle must be strong enough to support a body in the x-ray scan zone without having any highly x-ray attenuating materials in the scanning zone.

One prior approach to meeting the objectives of having low and uniform x-ray attenuation and adequate patient supporting strength in the cradle was to make the cradle basically from wood which had a curved cross section and relatively thick and large radius edges. The wood was painted or covered with a plastic skin for esthetic purposes. Molded plastic cradles having substantially the same configuration as the wood cradles were also used in connection with some computerized tomography scanners. In either case, however, it was necessary to support the cradle or table top near its end beyond the scanning zone in order to avoid the deflection which would otherwise occur if the patient's body was being supported on the cradle in cantilever fashion.

Besides having strength and x-ray attenuation problems, prior art table tops or cradles used in computerized tomography were required to have rather blunt edges which resulted in substantial transitions from low x-ray attenuation to a little higher attenuation as the scanning beam passed from a path wherein it penetrated air or body tissue to a path wherein it penetrated body tissue and the cradle. This transition of the beam in and out of the cradle edge resulted in streaks appearing in the visible display of the reconstructed x-ray image of a body layer.

Another problem with prior art patient supporting cradles is that their x-ray attenuation causes significant undesirable x-ray beam hardening. This results from the fact that when the x-ray beam from the source is in a scanning position wherein it penetrates the cradle before going through the body, low energy x-radiation composing the beam is absorbed in or filtered out of the beam by the cradle or table top and the remaining radiation which penetrates the body has proportionally more high energy x-radiation. When the scanner turns 180°, for instance, the opposite is true. That is, all of the high energy and low energy radiation in the beam is present for being attenuated by the body tissue and bony structures. The x-ray detectors, of course, are incapable of distinguishing between the two conditions and are likely to yield different analog signal values for different directions of the x-ray beam through similar paths. The ultimate result is small but erroneous density variations in the picture elements of the displayed image.

SUMMARY OF THE INVENTION

An object of the present invention is to provide a patient cradle which minimizes the aforementioned problems in that it has adequate strength for supporting a patient solely in cantilever fashion in the scanning x-ray beam with minimum deflection and yet has low x-ray attenuation, good patient comfort qualities sharp low contrasting edges, and low beam hardening effect.

Briefly stated, the new cradle comprises an elongated member composed of a rigid structural foam core which has a substantially crescent-shaped cross section. The edges of the core have a very small thickness or radius and there is a gradual increase in core thickness proceeding from the edges toward the center. A vacuum drawn skin comprised of fabric and fiber filler embedded in resin is vacuum formed on the core to produce a composite cradle. The skin edges have an even smaller radius or thickness than the foam core edges.

How the foregoing and other more specific objects of the invention are achieved will become evident in the ensuing more detailed description of a preferred embodiment of the invention which will now be set forth in reference to the drawings.

DESCRIPTION OF THE DRAWINGS

FIG. 1 is a perspective view showing a patient supported on the new cradle in readiness for being translated longitudinally into the scan zone of an adjacent typical computerized tomography scanner;

FIG. 2 is a plan view of the patient supporting cradle with parts broken away to show its interior construction;

FIG. 3 is an end elevation of the cradle viewed in the direction of the arrows 3—3 in FIG. 2 and FIGS. 4, 5 and 6 are transverse sections taken on lines corresponding with 4—4, 5—5 and 6—6 in FIG. 2; and FIG. 7 is a plan view of a mechanism for extending the fragmentarily shown cradle from its supporting base into the scan zone of the scanner.

DESCRIPTION OF A PREFERRED EMBODIMENT

A computerized axial tomography system in which the new patient cradle may be used is shown diagrammatically in FIG. 1. The patient support comprises a base 10 with a top section 11 that can be raised and lowered for positioning a patient at an elevation within the image reconstruction zone of the scanner for a tomographic scan. One end of the new crescent-shaped cradle 13 is visible in FIG. 1. As will be explained, the cradle 13 is translatable longitudinally to support a patient 14 in cantilever fashion in the active zone or circular reconstruction zone of a computerized tomography (CT) scanner. The scanner housing is indicated generally by the reference numeral 15. A source 16, shown schematically in dashed lines, of penetrating radiation such as x-radiation or gamma radiation is mounted for orbiting around the patient to effect an x-ray beam scan. The terms x-ray and x-ray source should be construed as embracing gamma rays and gamma ray sources as well as x-ray and x-ray sources for the purposes of this disclosure. An x-ray detector 17, shown schematically and in dashed lines, is also located inside of housing 15 for orbiting jointly and in fixed angular relationship around the patient with the x-ray source. The detector is a known type comprised of an array of adjacent individual detector cells. The x-ray beam, by way of example, emanates from a focal spot 18 in x-ray source 16 and is collimated into a thin diverging or fan-shaped beam which is intercepted by detector 17 after the beam is differentially attenuated by having passed through the patient.

Scanner housing 15 is provided with a circular shroud 19 in which there is a circular opening 21 that is large enough to permit the patient, while being supported on cradle 13, to be translated through it in contemplation of scanning successive layers of the body. The boundary rays of the thin fan-shaped beam are marked 22 and 23. A circular zone fitting well within boundary rays 22 and 23 is known as the image reconstruction circle and it is of sufficient size to encompass the patient.

The fan-shaped x-ray beam is somewhat more divergent than would be required for obtaining tangency to the reconstruction circle so that rays immediately inside of and next to the boundary rays 22 and 23 can pass by the patient and the cradle and go directly to some of the cells in the detector 17 which are used for obtaining reference signals which can be used for continuous calibration and for normalizing the attenuation data on which image reconstruction is based. In this way x-ray beam intensity variations which might occur during a scan can be compensated.

At this juncture, it is worthwhile to note that some of the rays in the fan-shaped x-ray beam must necessarily pass the laterally spaced apart edges of the elongated cradle 13 so that there will be a marked change in x-ray attenuation at the cradle edges which, in prior table designs was a major contributor to the occurrence of streaking in the reproduced x-ray image. As will be elaborated later, the new cradle is shaped in a manner which results in any streaks, which might have a tendency to occur, being outside of the reconstruction circle so they do not obscure diagnostic information in the displayed image.

X-ray source 16 and multiple-cell x-ray detector 17 are mounted for rotation or orbiting on a gantry, not shown, which is enclosed within housing 15. A suitable gantry is described in greater detail in U.S. Pat. No. 4,112,303, issued Sept. 5, 1978. The new cradle 13, of course, may be used with computerized tomography scanner systems which translate the radiation source and detector linearly and then rotate the source and detector jointly and translate again until the x-ray beam has swept through a semicircular path at least.

A plan view of the new cradle is shown in FIG. 2 and an end view and various cross sections are shown in FIGS. 3-6. In reference to FIG. 2, by way of example and not limitation, a typical cradle 13 may have a length of about seven feet or a little more and an overall width from edge to edge of about a foot. On its top surface in FIG. 2, one may see that the cradle has a pair of longitudinally spaced apart transverse lines 25 and 26 marked on it. These lines are the boundaries of an axially extending area which must be clear throughout the thickness of the cradle of any material which would attenuate x-rays by a significant amount since the part of the patient which lies between these lines is subjected to scanning.

Referring to FIG. 2, the cradle basically comprises a skin 28 which is bonded to a core 27 composed of rigid low x-ray attenuating structural foam. Acrylic foam is one example of a suitable foam. The foam core 27 has end pieces 29 and 30 bonded to it and these pieces are preferably made of a solid and strong material such as plastic or metal. When the foam core 27 is being formed, a rigid block 31 of a material such as phenolic is set in the mold for becoming embedded in the foam. The block has a groove 32 which is lined with the skin 28 material and serves as a hand hole for gripping the cradle when it is desired to advance and retract it longitudinally in a manual fashion. Block 31 with its hand engageable groove 32 and part of the foam core 27 surrounding it may be seen in the FIG. 4 sectional view. Another pair of longitudinally extending blocks 35 and 36 are also embedded in the foam core when it is being molded. As can be seen in FIG. 5, a typical block 35 has a central hole 36 which lies under a slot 37 in skin 28. As can be seen in FIG. 2, metal hold down plates 38 and 39 are set in slots 33 and 33'. Plates 38 and 39 have holes such as the one marked 40 which receive flat head studs for holding the cradle to an underlying longitudinally translatable carriage which will be described later in connection with FIG. 7.

As shown in FIG. 6, end member 30 has a portion 30' embedded in the end of foam core material 27 to provide for closing and finishing and stiffening the end of the cradle and for mounting a calibration phantom, not shown, on the cradle for purposes which are well-known to those involved in the CT art.

The cradle depicted in FIGS. 1-6 is made by molding the foam core 27 with the blocks 31, 35 and 36 and the end piece 30 embedded in it. As can be seen in FIGS. 3-6, the core 27 has a basically crescent shaped cross section. The skin 28 is applied all around the core by a molding process which involves wrapping the uncured skin around the core and heating the skin while the composite core and skin are disposed in a vacuum bag which conforms the skin to the core and effectuates bonding of the skin to the core. After the skin is applied and cured, the exposed surface of the skin is coated with any suitable coating such as white paint which has no x-ray attenuating heavy metal compounds in it. The lines 25 and 26 which mark the length of the active scanning area are then painted or otherwise inscribed on the top skin surface as shown in FIG. 2.

The skin 28 used in the preferred embodiment comprises thin layers of fabric with unidirectional fibers and alternate layers of carbon filaments or fibers laid up in an uncured epoxy base. The composite skin, of course, cures and solidifies when subjected to the heat associated with the process of forming it onto the foam core. Instead of using carbon fibers in the skin layers, fibers known by the DuPont trademark Kevlar may be used. The skin thickness is in the range of 0.02 to 0.08 of an inch. One may note in FIG. 5, for example, that when a skin 28 is formed on the core, the edges 28' and 28" are quite sharp which is an objective attained with the new cradle. In a commercial embodiment, these edges typically have a radius in the range of 0.03 to 0.05 of an inch. The rigid cured skin protects the edges of the core against fracture.

From inspection of FIGS. 3-6, for example, one may see that the radii of the upper and lower surfaces of the crescent-shaped cradle are different and that they are arc portions of respective circles. A radius of about 12 inches was chosen for the top surface as this was considered to be best for maximizing patient comfort. The bottom surface, by way of example and not limitation, has a radius of 7.75 inches. The different radii of the top and bottom surfaces result in the nominally crescent-shaped cross sectional configuration which the cradle has. In the same commercial embodiment, the width of the cradle from edge 28' to edge 28" is about 12.5 inches by way of example. The radius of the bottom surface of the crescent is just about equal to the radius of the image reconstruction circle which was mentioned earlier in connection with FIG. 1. Thus, the rays in the fan-shaped x-ray beam which are just tangent to the reconstruction circle may also be tangent to the lower surface of the cradle so, as an attempt is being made to show in FIG. 3, the rays 41 which would tend to cause streaks in the reconstructed image will lie outside of the image reconstruction circle.

The cradle depicted in FIGS. 1-6 is mounted on the elevator housing 11 in the table assembly shown in FIG. 1 and this housing contains the mechanism for translating the patient supporting cradle into and out of the x-ray beam and reconstruction circle as is required for making tomographic scans. The main components of an illustrative mechanism are depicted in FIG. 7. The mechanism includes a carriage plate 45 and a fragment of the cradle is shown secured to this plate by means of the hold down bars 38 and 39 and some flat head studs 46. The carriage has rollers such as those marked 47, 48 and 49 which run on tracks 50 and 51. The tracks are supported on a frame 52. The bottom of the carriage has an internally threaded lead screw nut 53 fastened to it. A lead screw 54 runs through the nut and is journaled to the frame in bearings 55 and 56. The lead screw has a shaft extension 57 on which there is a pulley 58 that is coupled by means of a belt 59 to another pulley 60 which is on the shaft of a reversible motor 61. It will be evident that rotation of the motor in opposite directions will turn the lead screw 54 correspondingly to cause longitudinal advancement and retraction of carriage 45 and cradle 13 which is supported thereon.

A bracket having a pair of arms 62 and 63 is fastened to one end of frame 52. The bracket supports a pair of spaced apart rollers 64 and 65 and another hourglass-shaped roller 66. The curved bottom of cradle 13 rests on these rollers and, since they are spaced away from the cradle carriage, they reduce the amount of cradle length that has to extend in cantilever fashion when the cradle is loaded with a patient and extended into the image reconstruction zone of the scanner.

I claim:
1. Computerized tomography apparatus including a scanner comprising a rotatable x-ray source for projecting a beam of x-radiation in a path transverse to a longitudinal axis on which an examination body may be disposed, x-ray detector means on a side opposite of the axis from the source for rotating coordinately with the source and for intercepting radiation that is attenuated by a body and emerges therefrom, a support and carriage means for supporting a table top on which a body may rest for being translated into and out of said x-ray beam path, and
  an improved composite table top characterized by permitting said top and any body thereon to be supported solely in cantilever fashion in said beam path, said top comprising:
  an elongated core comprised of rigid structural foam having low x-ray attenuating properties and having top and bottom surfaces which have different radii of curvature resulting in said core having a nominally crescent-shaped cross section and in said surfaces intersecting to produce relatively sharp and thin longitudinally extending laterally spaced apart edges,
  a skin bonded to said core and composed of high strength fibers entrained in heat curable resin and having low x-ray attenuating properties, said skin covering said core including said edges and having a thickness that results in minimal increase in the thickness of said edges,
  means for mounting said composite top to said carriage means to enable a substantial part of the length of said top to extend in cantilever fashion from said carriage means,
  said x-ray beam being nominally planar and said longitudinal axis being substantially perpendicular to the plane of the beam and said beam being divergent in said plane from said source to said detector means, predetermined angularly separated diverging rays in said beam being tangent to a circular x-ray image reconstruction zone to which said axis is also substantially perpendicular,
  said lower surface of said table top having a radius of curvature substantially equal to the radius of said circle and said curvature and circle being concentric so that when said table top is in said beam path and said beam is rotated for projecting laterally and from below said lower surface said predetermined rays will be substantially tangent to the circle of which said bottom surface is an arc portion and rays outside of the angle between said predetermined rays which could cause streaks in the image will be outside of the reconstruction circle.
2. The table top in claim 1 wherein the radius of said top surface is on the order of 12 inches, the radius of said bottom surface is about 7.75 inches and the shortest distance between said edges is about 12.5 nches.

* * * * *